United States Patent
Lewis et al.

(10) Patent No.: US 8,808,390 B2
(45) Date of Patent: Aug. 19, 2014

(54) ACETABULAR PROSTHESIS HAVING AN ORIENTABLE FACE

(75) Inventors: Paul Peter Lewis, Warsaw, IN (US); James Alan Caywood, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1310 days.

(21) Appl. No.: 11/904,479

(22) Filed: Sep. 27, 2007

(65) Prior Publication Data
US 2009/0088864 A1 Apr. 2, 2009

(51) Int. Cl.
*A61F 2/34* (2006.01)

(52) U.S. Cl.
USPC ............... 623/22.25; 623/22.18; 623/22.28; 623/22.19; 623/22.35

(58) Field of Classification Search
None
See application file for complete search history.

(56) References Cited

U.S. PATENT DOCUMENTS

| | | | |
|---|---|---|---|
| 4,678,472 A | 7/1987 | Noiles | |
| 4,695,282 A | 9/1987 | Forte et al. | |
| 4,704,127 A | 11/1987 | Averill et al. | |
| 4,883,491 A | 11/1989 | Mallory et al. | |
| 4,978,356 A | 12/1990 | Noiles | |
| 5,002,577 A | 3/1991 | Bolesky et al. | |
| 5,019,105 A | 5/1991 | Wiley | |
| 5,049,158 A | 9/1991 | Engelhardt et al. | |
| 5,226,917 A | 7/1993 | Schryver | |
| 5,310,408 A | 5/1994 | Schryver et al. | |
| 5,358,532 A | 10/1994 | Evans et al. | |
| 5,413,603 A | 5/1995 | Noiles et al. | |
| 5,571,198 A | 11/1996 | Drucker et al. | |
| 5,658,347 A | 8/1997 | Sarkisian et al. | |
| 5,702,477 A | 12/1997 | Capello et al. | |
| 5,782,928 A | 7/1998 | Ries et al. | |
| 5,879,401 A * | 3/1999 | Besemer et al. | 623/22.28 |
| 5,935,175 A | 8/1999 | Ostiguy, Jr. et al. | |
| 6,527,809 B1 | 3/2003 | Doursounian et al. | |
| 2005/0021148 A1 * | 1/2005 | Gibbs | 623/22.12 |
| 2006/0167556 A1 * | 7/2006 | Lazennec et al. | 623/22.24 |
| 2006/0190089 A1 * | 8/2006 | Montoya et al. | 623/22.28 |
| 2007/0106389 A1 * | 5/2007 | Croxton et al. | 623/22.17 |

FOREIGN PATENT DOCUMENTS

| | | | |
|---|---|---|---|
| DE | 196 16 059 A1 | 10/1997 | |
| EP | 0 773 007 A1 | 5/1997 | |
| EP | 0807426 | 11/1997 | |
| EP | 1082949 A1 * | 3/2001 | A61F 2/34 |
| EP | 1384456 | 1/2004 | |
| EP | 1532946 | 5/2005 | |

OTHER PUBLICATIONS

European Patent Office, European Search Report, Application—EP 08 16 4945, Jan. 30, 2009, 2 pages.

* cited by examiner

*Primary Examiner* — Thomas J Sweet
*Assistant Examiner* — Rebecca Preston
(74) *Attorney, Agent, or Firm* — Maginot, Moore & Beck, LLP

(57) ABSTRACT

A prosthetic component assembly, such as an acetabular cup, includes a shell, a bearing positioner and a bearing. The shell and bearing positioner are configured to facilitate orienting the bearing positioner in multiple orientations relative to the shell and for securing the bearing positioner in a selected orientation of the multiple orientations relative to the shell. The bearing is configured to be received in the bearing positioner at multiple rotational orientations for optimal joint biomechanics. The bearing positioner is selected from among a plurality of lateralized positioners to accommodate the joint anatomy.

13 Claims, 12 Drawing Sheets

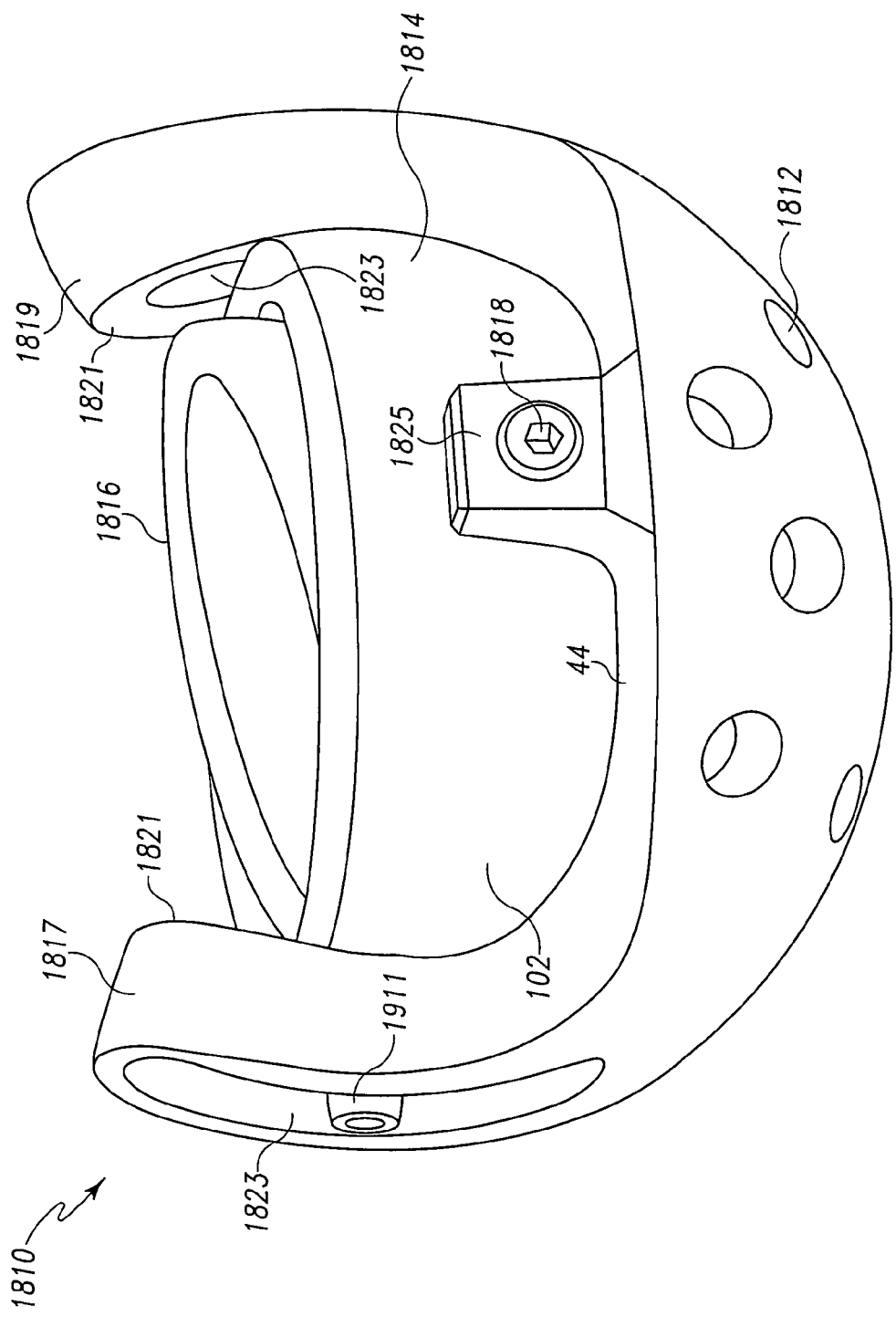

ACETABULAR PROSTHESIS HAVING AN ORIENTABLE FACE

BACKGROUND

The present invention is directed to a prosthetic cup assembly that is disclosed in the context of a hip prosthesis and more particularly to such an assembly that permits the prosthesis to be implanted at a desirable fixation point in the hip while allowing the face of the bearing surface to be oriented independently of the implant position within the acetabulum.

It is known to provide an acetabular cup assembly that includes a metal shell component for attachment to an acetabulum to replace the natural socket and a bearing component (commonly made of plastic, metal or ceramic) that is inserted into the shell to provide a bearing surface for receiving a femur ball prosthesis element or the proximal end of the femur head. See for example, Englehart et al., U.S. Pat. No. 5,049,158, the disclosure of which is expressly incorporated herein by reference. In addition, traditional bearing components include a built-up lip around a portion of the bearing surface. See for example, U.S. Pat. Nos. 5,282,864 and 5,413,603 to Noiles et al., the disclosures of which are also expressly incorporated herein by reference.

A problem that can occur with such acetabular cup assemblies is that they are configured so that the shell needs to be implanted in a very specific location in the acetabulum in order for the bearing surface to present a desirable surface for the head of the femur ball prosthesis to ride against in order to simulate the patient's natural anatomical structure and range of motion.

Some acetabular cup assembly designs have used a third member as a way to maintain macrostability of the assembly parts while maintaining dome loading. Dome loading designs essentially ensure contact in the dome region by leaving clearance under the lip of the liner. These dome loading designs however, cause the insert to seat in the direction of the applied load.

The shape and orientation of the concave face of the acetabular shell and the shape of the convex mating surface of the bearing received therein establish the orientation of the bearing face of the bearing when it is received in the acetabular shell. Once an acetabular shell is fixed in place, the orientation of the concave face of the acetabular shell, and therefore the bearing face of the bearing, can not be changed without disrupting the bone shell interface. Face changing poly liners do offer some measure of adjustment, but this option is not available for all bearings. The bearing face position is largely dictated by the position of the shell since they typically cannot be positioned independent of one another.

Two currently available ways to change the bearing face orientation of the bearing is to use a face changing bearing (if available) or remove the shell thereby disrupting the shell bone interface, and repositioning the shell. Face changing liners do not always offer enough change.

SUMMARY

The disclosed acetabular prosthesis provides a bearing positioner for an acetabular reconstruction device including a shell and a bearing that positions the bearing independent of the shell position. According to one aspect of the disclosure, an acetabular prosthetic device for attachment to a hip comprises a shell, a bearing positioner and a position fixation device. The shell is configured for attachment to the hip and includes a concave surface configured to face away from the hip. The concave surface defines a bearing positioner-receiving cavity. The bearing positioner includes a convex surface and a concave surface. The convex surface is configured to be received in the bearing positioner-receiving cavity and oriented in multiple angular positions relative to the shell. The concave surface faces in the opposite direction as the convex surface and defines a bearing-receiving cavity. The position fixation device is configured to affix the bearing positioner to the shell in a selected position of the multiple angular positions.

According to another aspect of the disclosure, bearing positioner is disclosed for utilization with a bearing having a convex surface and an oppositely facing bearing surface configured to bear against a first bone of a joint or prosthetic replacement for a portion of the first bone and a prosthetic component configured for attachment to a second bone of the joint which prosthetic component includes a bone facing surface configured to face the second bone and a concave surface facing away from the bone facing surface and defining a cavity.

The bearing positioner comprises an external convex surface and an internal concave surface. The external convex surface has a shape configured to be received in the cavity in multiple orientations and to bear and be secured against the concave surface of the prosthetic component when in any orientation selected from the multiple orientations. The internal concave surface defines a bearing-receiving cavity configured to receive a portion of the convex surface of the bearing therein and configured to orient the bearing surface of the bearing to bear against the first bone of the joint or the prosthetic replacement for the first bone when the external convex surface of the bearing positioner is secured in an orientation selected from the multiple orientations.

According to still another aspect of the disclosure, a method of assembling a prosthetic component assembly is disclosed. The method includes: (a) providing a shell having a cavity with an inner surface, the inner surface having a shape; (b) providing a bearing positioner having an outer surface with a shape corresponding to the shape of the inner surface of the shell and an oppositely facing concave surface defining a bearing-receiving cavity; (c) inserting a portion of the bearing positioner into the cavity of the shell; (d) angulating the bearing positioner relative to the shell after inserting the portion of the bearing positioner into the shell to position the bearing positioner in a desired angular relationship relative to the shell; (e) securing the bearing positioner to the shell in the desired angular relationship relative to the shell; (f) providing a bearing having a convex surface configured for receipt in the bearing-receiving cavity and an oppositely facing bearing surface configured to engage and allow a head of a bone or a prosthetic replacement for a head of a bone to articulate thereagainst; and (g) inserting the bearing into the bearing-receiving cavity so that at least a portion of the convex surface of the bearing engages at least a portion of the concave surface of the bearing positioner and the bearing surface is oriented to facilitate articulation of the head of a bone or a prosthetic replacement for a head of a bone to articulate thereagainst when the bearing positioner is secured to the shell in the desired angular relationship relative to the shell.

The disclosed embodiments permit mechanical attachment of the bearing to the shell of a prosthetic joint component with the bearing selectively positionable relative to the shell. Thus, in accordance with certain features of the disclosed embodiments, the bearing may be angled with a fixed range of angles relative to the shell surface, the high point of the angled bearing face may be infinitely positioned rotationally about an axis perpendicular to the shell surface, and the center of articulation of the bearing may be positioned at a pre-determined distance away from the outside surface of the shell. The bearing positioner disclosed herein provides these three positioning characteristics. With respect to the latter positioning characteristic, adjustment of the location of the center of articulation may be accomplished by lateralization of the internal concave surface.

The bearing positioners disclosed herein thus allow the shell to be fixed to the bone in the optimal position for bone/shell attachment, and the bearing to be placed in the optimal position for hip biomechanics, all independent of each other. The bearing positioners allow positioning of the bearing relative to the shell in three distinct ways: 1) the bearing face may be angled within a fixed range relative to the shell interior surface; 2) the high point of the angled bearing face may be infinitely positioned rotationally about an axis perpendicular to the shell interior surface; and the bearing articulation center or focus may be positioned at pre-defined distances from the center or focus of the shell outer surface.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

The illustrative devices will be described hereinafter with reference to the attached drawings which are given as non-limiting examples only, in which:

FIG. 19 is a perspective view of a second embodiment of an acetabular cup assembly showing a third embodiment of a shell, a second embodiment of a bearing positioner and a second embodiment of a bearing.

Corresponding reference characters indicate corresponding parts throughout the several views.

DETAILED DESCRIPTION

Figure 1:
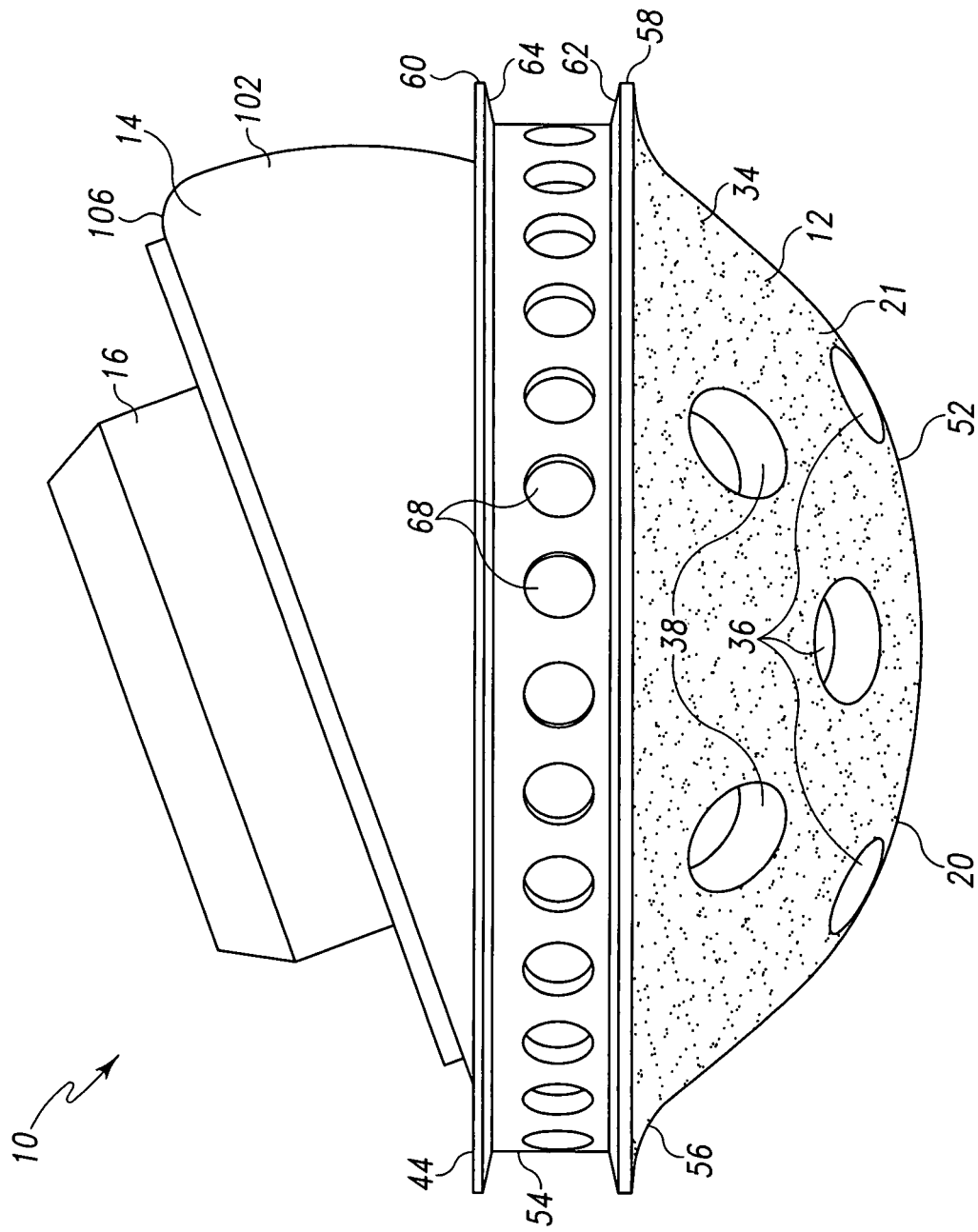
FIG. 1 is a perspective view of an acetabular cup assembly including a first embodiment of a shell, a first embodiment of a bearing positioner and a first embodiment of a bearing with the bearing positioner positioned relative to the shell to position a face of the bearing at approximately a twenty degree angular offset relative to a neutral position.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIGS. 1-16, an acetabular reconstruction device 10 is shown. The acetabular reconstruction device or prosthesis includes a shell or hub 12, a bearing positioner 14, a bearing 16 and a screw 18. While only a single hub 12, bearing positioner 14 and bearing 16 is shown, those skilled in the art will recognize, that a plurality of differently sized and configured shells 12, bearing positioners 14 and bearings 16 may be provided to facilitate matching the components with the anatomy of the patient into which the prosthesis 10 will be implanted.

For instance, it is a common practice to provide multiple differently configured bearings that are each adapted to mate with a single shell to provide different positional orientation of the face of the bearing when the bearing is received in the shell. Similarly, it is within the scope of the disclosure to provide multiple differently configured bearings 16 that are each adapted to mate with a given bearing positioner 14 to provide different positional orientation of the face of the bearing 16 when the bearing 16 is received in the bearing positioner 14. The described bearing 16 should be considered to be a "neutral" bearing 16 providing a face orientation consistent with a common anatomical structure of a patient.

Similarly, it is a common practice to provide multiple differently configured shells each sized to provide optimal bone to prosthesis contact for a common size of hip bone. The disclosed shell 12 therefore should be considered as an exemplary shell 12 configured for implantation into a standard sized hip. Differently sized shells 12 may be provided within the scope of the disclosure for utilization with patients having differently sized hips.

In the illustrated embodiment, the shell 12 includes an external convex surface 20 and an internal concave surface 22. The convex surface 20 and concave surface 22 are illustratively, at least in part, semispherical, i.e. substantial portions of the surface are equidistant from a focus 24. Illustratively, the semispherical portion 21 of the convex surface 20 and the semispherical concave surface 22 are each formed about a common focus 24. In the illustrated embodiment, the semispherical portion 21 of the convex surface 20 exhibits a radius of curvature 26 and the semispherical concave surface 22 exhibits a radius of curvature 28 differing from the radius of curvature 26 of the semispherical portion 21 of the convex surface 20.

The radius of curvature 26 of the semispherical portion 21 of the convex surface 20 is sized to approximate the curvature of the acetabulum of the hip of the patient into which the acetabular prosthesis 10 is to be implanted. In the illustrated embodiment, the radius of curvature 26 of the semispherical portion 21 of the convex surface 20 is approximately 1.196 inches. As mentioned previously, it is within the scope of the disclosure for the multiple differently configured shells 12 to be provided each having a different radius of curvature 26 of the semispherical portion 21 of the convex surface 20 so that the surgeon can select a shell 12 for implantation that will have the optimal configuration for stably implanting the shell 12 in the hip of the patient. Also, it is within the scope of the disclosure for the external convex surface of the shell 12 to have a different shape which would facilitate implantation into the hip of the patient and such surface shape is not limited to including a semispherical portion.

The radius of curvature 28 of the semispherical concave surface 22 is sized to approximate the curvature of an external convex surface 102 of a bearing positioner 14, to facilitate mating of the bearing positioner 14 to the shell 12. Since it is within the scope of the disclosure for multiple bearing positioners 14 to be provided each having a differently sized convex surfaces 102, it is within the scope of the disclosure for the radius of curvature 28 of the concave surface 22 to assume different values corresponding to the curvature of the corresponding convex surface 102 of the bearing positioner 14 with which the shell 12 is to mate. The radius of curvature 28 of the semispherical concave surface 22 of the illustrated and described shell 12 is approximately 1.073 inches to facilitate mating with the illustrated and described bearing positioner 14.

The concave surface 22 of the shell 12 defines a bearing positioner-receiving cavity 30 sized and configured to receive a portion of a bearing positioner 14 therein for mating to form a portion of the acetabular prosthesis 10. While being described as a concave surface 22 it is within the scope of the disclosure for the shell 12 to include a differently sized and shaped surface configured to facilitate mating the bearing positioner 14 to the shell 12. For instance the mating surface 22 of the shell 12 may be convex and be configured to mate with a concave mating surface 102 of a bearing positioner 14 within the scope of the disclosure. The concave surface 22 is described as being semispherical as this shape appears to provide the optimal shape to permit the shell 12 to mate with a bearing positioner 14 having a semispherically shaped convex mating surface 102 while permitting the bearing positioner 14 to be oriented in different positions relative to the shell 12 as will be explained further below.

The shell 12 is configured for attachment to the acetabulum. The shell 12 attaches to the acetabulum with or without the aid or one or more adjunct fixation devices such as screws, spikes, flanges, bubbles, etc. The illustrated shell 12 includes attachment features 32 configured to facilitate attachment of the shell 12 to an acetabulum. Among the illustrated attachment features 32 are a bubbled surface 34, a plurality of bone screw apertures 36, a plurality of in-growth apertures 38 and an annularly extending fixation device attachment channel 40. It is within the scope of the disclosure for any of the shells 12, 1712, 1812 disclosed herein to include any of the illustrated attachment features 32 or additional non-illustrated attachment features 32 such as spikes, pins, flanges, keels, annular rings or partial annular rings and other projections. Among the patents illustrating a few of such attachment features are U.S. Pat. Nos. 4,883,491; 5,226,917; 5,310,408; 5,358,532; 5,658,347; and, 5,702,477, the disclosures of which are all incorporated herein by this reference.

The convex surface 20 of the shell 12 is textured with a bubbled or porous coating 34 to facilitate securing shell 12 in place within an appropriately prepared acetabulum. The porous coating 34 is configured to facilitate biological ingrowth of a patient's bone within the outer surface of the shell 12 whereby long-term fixation of the shell 12 to the patient's bone may be achieved. A number of spikes (not shown) may be secured to the outer surface of the shell 12 to further facilitate fixation of the shell 12 to the patient's bone as is well known in the art. Use of such a bubbled or porous coating 34 is well known in the art and such a coating 34 is utilized to facilitate bone in-growth and on-growth with the implanted shell 12. In the illustrated embodiment, shell 12 is preferably made from titanium, but may be made from a cobalt chrome material or other suitable materials. The type of porous coating 34 utilized is selected from those coating materials known to adhere or bond well to the material from which the shell 12 is fabricated. Alternatively, the shell 12 may be sand blasted or otherwise roughened to provide the textured finish 34.

The illustrated embodiment of shell 12 includes a plurality of bone screw holes 36 (illustratively six) extending between the convex surface 20 and the concave surface 22. The bone screw holes 36 are configured for receipt of bone screws therethrough to aid in securing the shell 12 to the hip of the patient in a known manner. The bone screw holes 36 are also configured to receive the head of a bone screw therein with the head positioned to avoid interference with orientation of the bearing positioner 14 within the bearing positioner-receiving cavity 30. Therefore, as shown, for example, in FIG. 9, adjacent the concave surface 22, the bone screw holes 36 are formed to include a feature 41, such as a countersink, to permit the head of the bone screw to be seated below the concave surface 22 of the shell 12.

In the illustrated embodiment, the six bone screw holes 36 are positioned equidistantly (sixty degrees apart) around the shell 12. The bone screw holes 36 are each displaced by the same angle 42 from the rim 44 of the shell 12. Illustratively, the angle 42 is approximately sixty degrees. Utilization of bone screw holes and bone screws for attachment of acetabular components to the hip of a patient is well known in the art and is described in greater detail in U.S. Pat. No. 5,571,198, the disclosure of which is incorporated herein by this reference. Those skilled in the art will recognize that whenever a bone screw is not received in a bone screw hole 36 of an implanted shell 12, the bone screw hole 36 may act as a situs for bone in-growth to help secure the shell 12 to the hip.

In the illustrated embodiment the rim 44 is a substantially planar wall extending between the convex surface 20 and the concave surface 22 perpendicular to the axis 82 of the shell 12. The rim 44 is displaced from the focus 24 by a displacement 45. In the illustrated embodiment, the displacement is approximately 0.273 inches.

The illustrated embodiment of shell 12 includes a plurality of in-growth apertures 38 (illustratively six) extending between the convex surface 20 and the concave surface 22. The plurality of in-growth apertures 38 are configured to allow the bone of a patient to grow therein to facilitate increased stability of the implant 10. As shown, for example, in FIG. 8, the walls 46 defining each of the plurality of in-growth apertures 38 are not cylindrically formed about the axis 48 of the aperture 38 but rather are concave with respect to the axis 48. The concavity of these walls 46 facilitates bone attachment to the shell 12 during in-growth into the plurality of in-growth apertures 38.

Those skilled in the art will recognize that any of the plurality of in-growth apertures 38 could alternatively be utilized as sites through which other fixation devices such as bone screws or pins are extended or bone cement is received to aid in securing the shell 12 in the desired location in the hip of the patient in a known manner. In the illustrated embodiment, the six in-growth apertures 38 are positioned equidistantly (sixty degrees apart) around the shell 12 and are angularly displaced by thirty degrees from each adjacent bone screw hole 36. Each of the in-growth apertures 38 is displaced by the same angle 50 from the rim 44 of the shell 12. Illustratively, the angle 50 is approximately forty-two degrees.

To this point, the bone facing surface 52 of the shell 12 has been described only with regard to the outer convex surface 20 which has been described as having a semispherical portion 21. The bone facing surface 52 of the illustrated shell 12 also includes a cylindrical wall portion 54, a transition region 56, a proximal annular outwardly extending lip 58 and a distal annular outwardly extending lip 60. The transition region 56 extends between the semispherical portion 21 of the convex surface 20 and the proximal lip 58 to provide a smooth transition between those features.

The proximal and distal lips 58, 60 are positioned on opposite edges of the cylindrical wall portion 54 of the bone facing surface 52. The inner wall 62 of the proximal lip 58, the inner wall 64 of the distal lip 60 and the cylindrical wall portion 54 cooperate to define the fixation device attachment channel 40. As shown, for example, in FIG. 7, the inner wall 62 of the proximal lip 58 and the inner wall 64 of the distal lip 60 slant away from each other as they extend from the cylindrical wall 54 to form a taper 66. Illustratively, the taper 66 between the inner walls 62, 64 of the lips 58, 60, respectively, is approximately twenty degrees. The taper 66 is provided to facilitate stable seating of an attachment flange 1702 of an adjunct fixation device 1700 such as that illustrated attached to the second embodiment of a shell 1712 in FIG. 18.

A plurality of attachment holes 68 extend between the cylindrical wall 54 and the concave surface 22 of the shell 12 to facilitate attachment of an adjunct fixation device 1700 to the shell 12. Adjacent the concave surface 22, each attachment hole is configured to include a counter bore 70 having a cylindrical wall 72 sized to receive the head of a fastener 1701 which seats against a ring shaped wall 74 extending between the cylindrical wall 72 and a shaft aperture 76. Adjacent the cylindrical wall portion 54 of the bone facing surface 52, each attachment hole 68 is formed to include a counter sink 78. When an adjunct fixation device 1700 is utilized with shell 12, the fastener 1701 is inserted into the attachment hole 68 so that the head is received in the counterbore 70 so as to not interfere with orientation of the bearing positioner 14 within the bearing positioner-receiving cavity 30. The threaded shaft of the fastener 1701 extends through the shaft aperture 76 and threadingly engages an internal thread formed in an attachment hole 1704 extending through the attachment flange 1702 of the adjunct fixation device 1700.

The shell 12 is formed to include a threaded bearing positioner attachment hole 80 extending between the concave surface 22 and the convex surface 20. The bearing positioner attachment hole 80 is an apex hole formed concentrically about the axis 82 of the shell 12. The bearing positioner attachment hole 80 is sized to receive the shaft 202 of the screw 18 therein to secure the bearing positioner 14 within the shell 12. The thread 84 of the bearing positioner attachment hole 80 is a conformal thread to the thread 204 on the shaft 202 of the screw 18.

As shown, for example, in FIGS. 1, 2, 3 and 10-14, the bearing positioner 14 includes a convex surface 102, a concave surface 104, and a rim wall 106 formed generally concentrically about an axis 110 and a screw-receiving slot 108. The bearing positioner 14 is preferably made from titanium, but may be made from a cobalt chrome material, or other suitable materials. The concave surface 104 defines a bearing-receiving cavity 112 configured to receive a portion of the bearing 16 therein. In the illustrated embodiment, the rim wall 106 extends between and couples the concave surface 104 and the convex surface 102.

In the illustrated embodiment the convex surface 102 is generally hemispherical and is formed concentrically about a focus 114. The convex surface 102 is sized and shaped to be received, at least in part, within the bearing positioner-receiving cavity 30 of the shell 12 and to allow the bearing positioner 14 to be oriented in a desired position with respect to the shell 12. Since the illustrated bearing positioner 14 is configured for use with the illustrated shell 12, the radius of curvature 116 of the convex surface 102 is approximately equal to the radius of curvature 28 of the concave surface 22 of the shell 12. In the illustrated embodiment, the radius of curvature 116 of the convex surface 102 is approximately 1.078 inches.

Those skilled in the art will recognize that the stated radius of curvature 116 of the convex surface 102 is slightly greater than (illustratively 0.005 inches) the stated radius of curvature 28 of the concave surface 22 of the shell 12. This slight difference between the radius of curvature 116 and the radius of curvature 28 induces the bearing positioner 14 to seat along a narrow equatorial strip of both the convex surface 102 of the bearing positioner 14 and the concave surface 22 of the shell 12 when the screw 18 urges the convex surface 102 into engagement with the concave surface 22. Since the radius of curvature 116 of the convex surface 102 of the bearing positioner 14 is somewhat larger than the radius of curvature 28 of the concave surface 22 of the shell 12, the equator regions of the two components load when the screw 18 is tightened maintaining a stable interface with little relative motion between the shell 12 and the bearing positioner 14.

The concave surface 104 of the bearing positioner 14 comprises a semispherical portion 118 at a radius of curvature 117 and a tapered portion 120 both formed concentrically about the axis 110. In the illustrated embodiment, the tapered portion 120 extends between and couples the semispherical portion 118 of the concave surface 104 and the rim wall 106. The rim wall 106 defines a plane through which the bearing 16 enters the cavity 112 of bearing positioner 14 formed by concave surface 104. The tapered portion 120 forms a female taper having a taper 121. The female taper extends around the entire periphery of cavity 112 adjacent the rim wall 106. It is understood that the axial depth of female taper within cavity 112 may vary. In the illustrated embodiment the taper 121 is approximately ten degrees and is configured to mate with a corresponding male taper on the bearing 16.

The bearing positioner 14 contains an apex hole that is elongated to one side sufficient to form the screw-receiving slot 108 to provide the desired amount of relative angular position between the shell 12 and the bearing positioner 14. When the screw 18 passes through screw-receiving slot 108 in the bearing positioner 14 and the attachment hole 80 in the shell 12, the bearing positioner 14 is able to angulate as allowed by the screw-receiving slot 108 and can be positioned rotationally by rotating about the head 200 of the screw 18.

Such rotational positioning is accomplished by rotating the bearing positioner 14 about the axis 82 of the shell 12 which coincides with the axis 212 of the screw 18 when the shaft 202 of the screw 18 is received in the attachment aperture 80 of the shell 12.

In the illustrated embodiment, the screw-receiving slot 108 is configured to permit approximately twenty degrees of angulation of the bearing positioner 14 relative to the shell 12. The illustrated screw-receiving slot 108 comprises a fastener-receiving slot 122 and a head-receiving slot 124.

The fastener-receiving slot 122 includes a first planar side wall 126 spaced apart from a second planar side wall 128 by a displacement 130. Illustratively, the displacement 130 is approximately equal to, or slightly greater than the diameter 210 of the shaft 202 of the screw 18 to allow the shaft 202 of the screw 18 to slide therein. The fastener-receiving slot 122 includes a first semi-cylindrical end wall 132 coupling one end of the first planar side wall 126 to the second planar side wall 128. The first semicylindrical end wall 132 has a radius of curvature 134 approximately equal to one half the diameter 210 of the shaft 202 of the screw 18 and is formed concentrically about the axis 110 of the bearing positioner 14. The fastener-receiving slot 122 includes a second semi-cylindrical end wall 136 coupling the other end of the first planar side wall 126 to the second planar side wall 128. The second semicylindrical end wall 136 has a radius of curvature 138 approximately equal to one half the diameter 210 of the shaft 202 of the screw 18 and is formed concentrically about an axis 140 extending radially from the focus 114 of the bearing positioner 14 at an angle 142. In the illustrated embodiment, the angle 142 is approximately twenty degrees.

Figure 3:
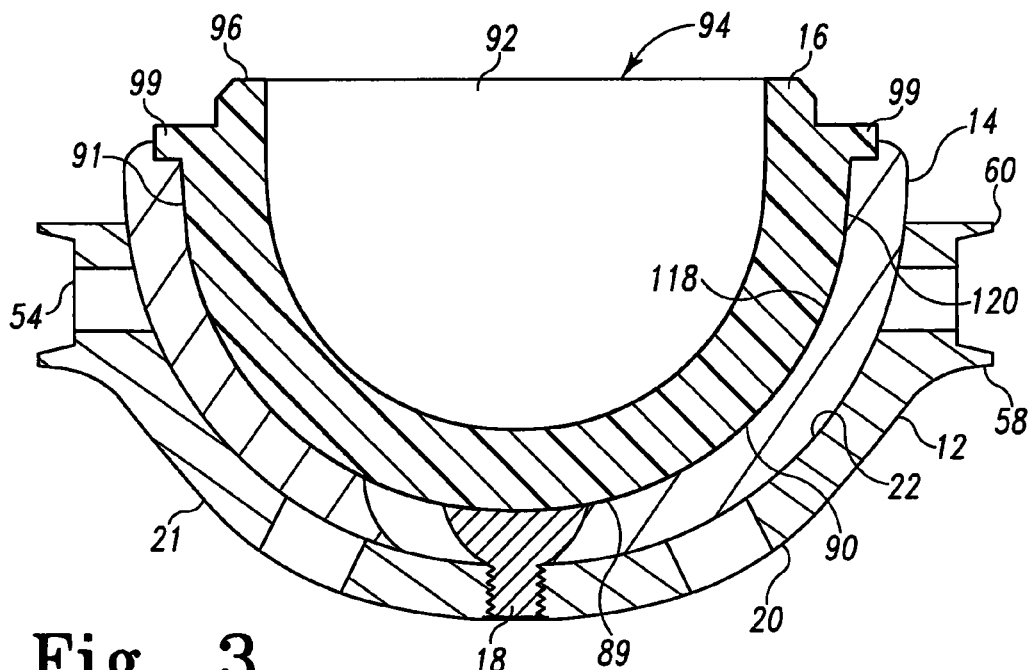
FIG. 3 is a sectional view of the acetabular cup assembly of FIG. 1 showing with the bearing positioner positioned relative to the shell to position a face of the bearing at a neutral position.
Figure 2:
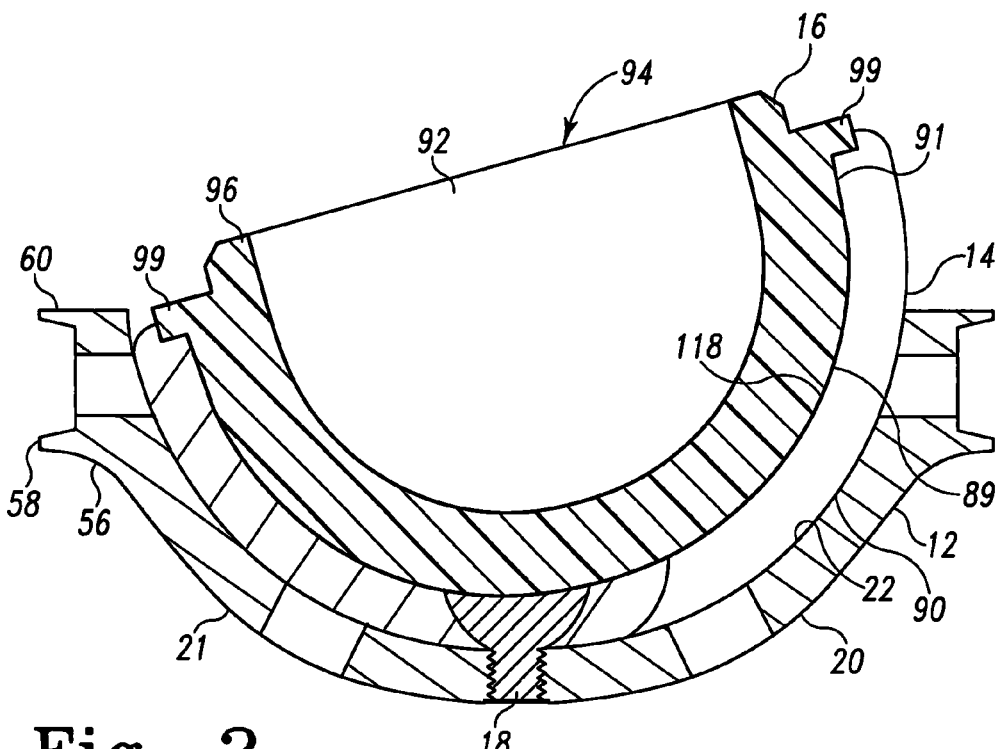
FIG. 2 is a sectional view of the acetabular cup assembly of FIG. 1 showing with the bearing positioner positioned relative to the shell to position a face of the bearing at approximately a twenty degree angular offset relative to a neutral position.
Figure 4:
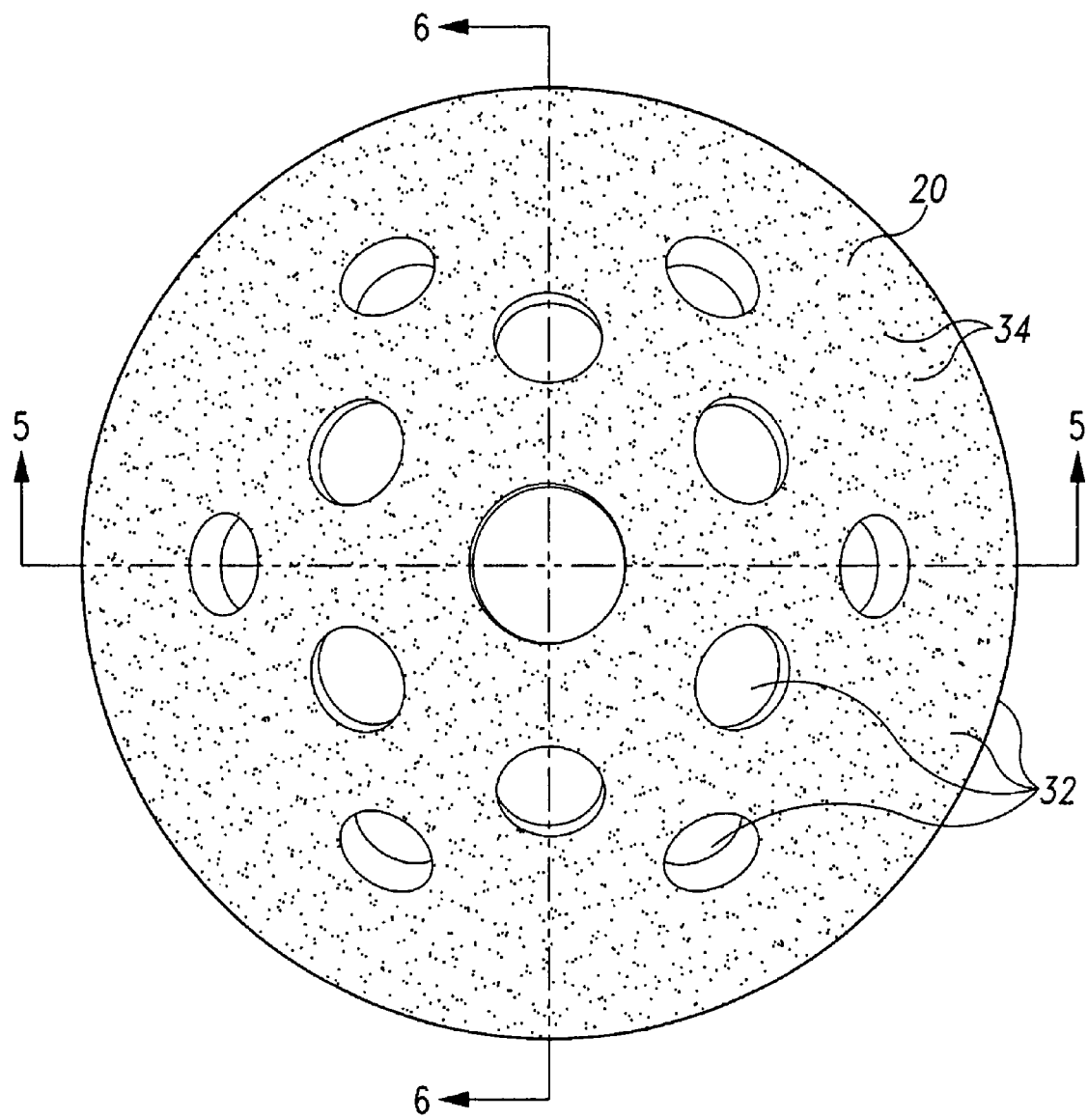
FIG. 4 is a plan view of the shell of the acetabular cup assembly of FIG. 1.
Figure 6:
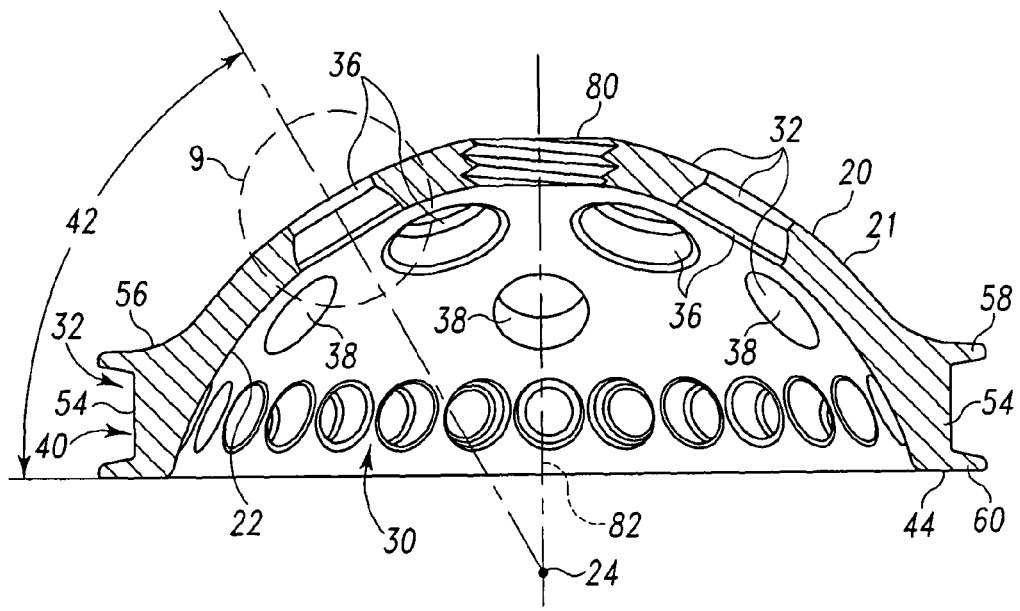
FIG. 6 is a sectional view taken along line 6-6 of the shell of FIG. 4.
Figure 5:
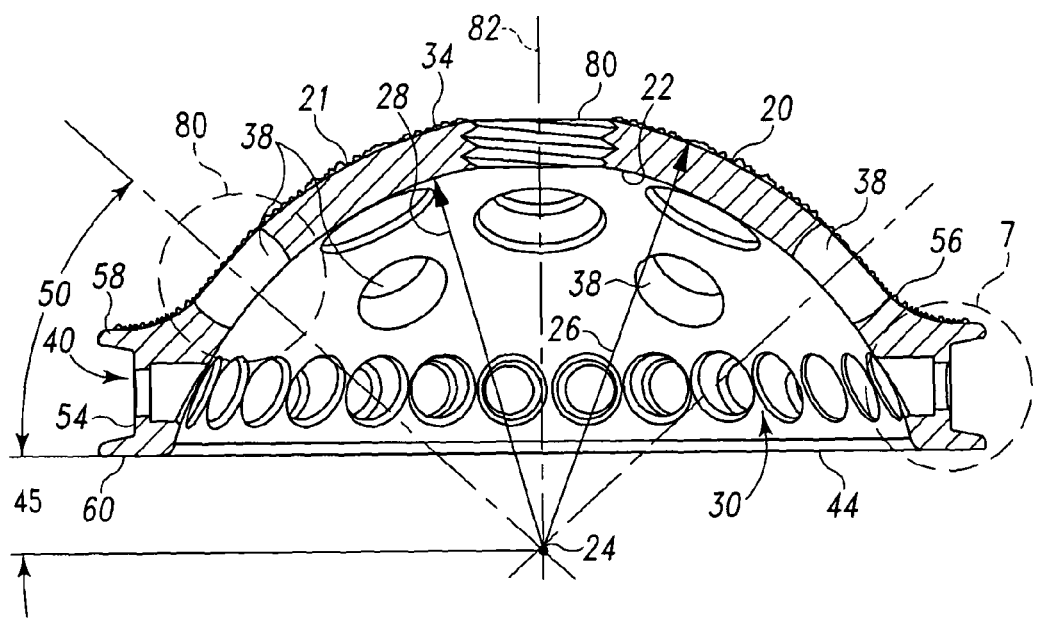
FIG. 5 is a sectional view taken along line 5-5 of the shell of FIG. 4.
Figure 7:
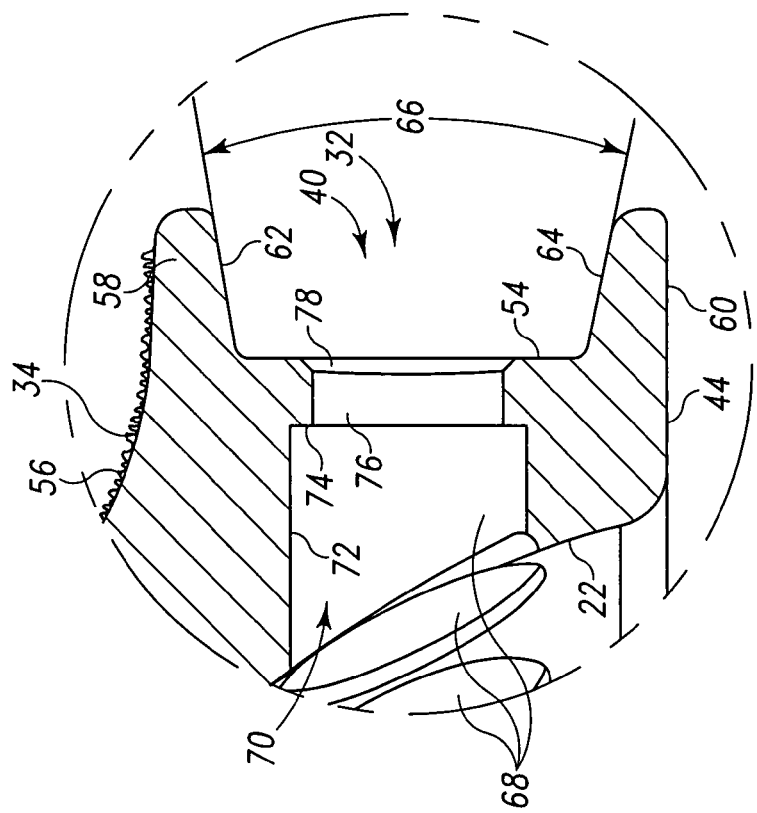
FIG. 7 is a view of that portion of the shell enclosed in circle 7 in FIG. 5.
Figure 8:
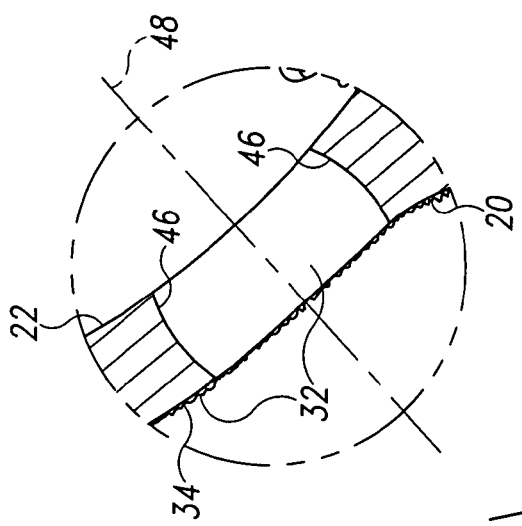
FIG. 8 is a view of that portion of the shell enclosed in circle 8 in FIG. 5.
Figure 9:
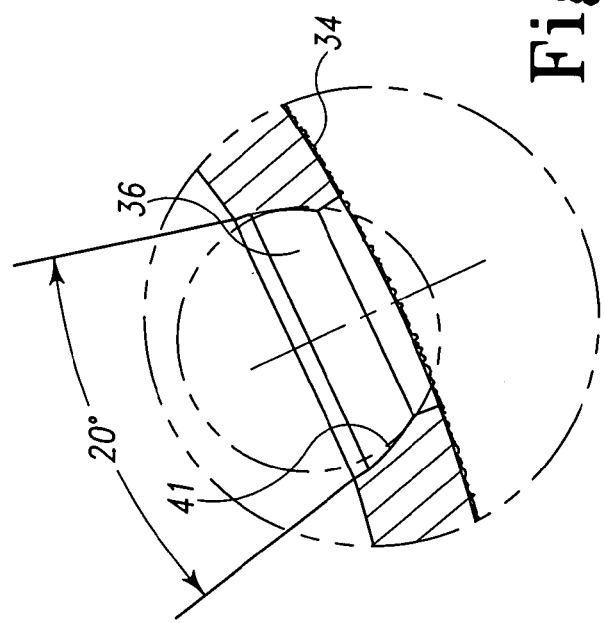
FIG. 9 is a view of that portion of the shell enclosed in circle 9 in FIG. 6.
Figure 10:
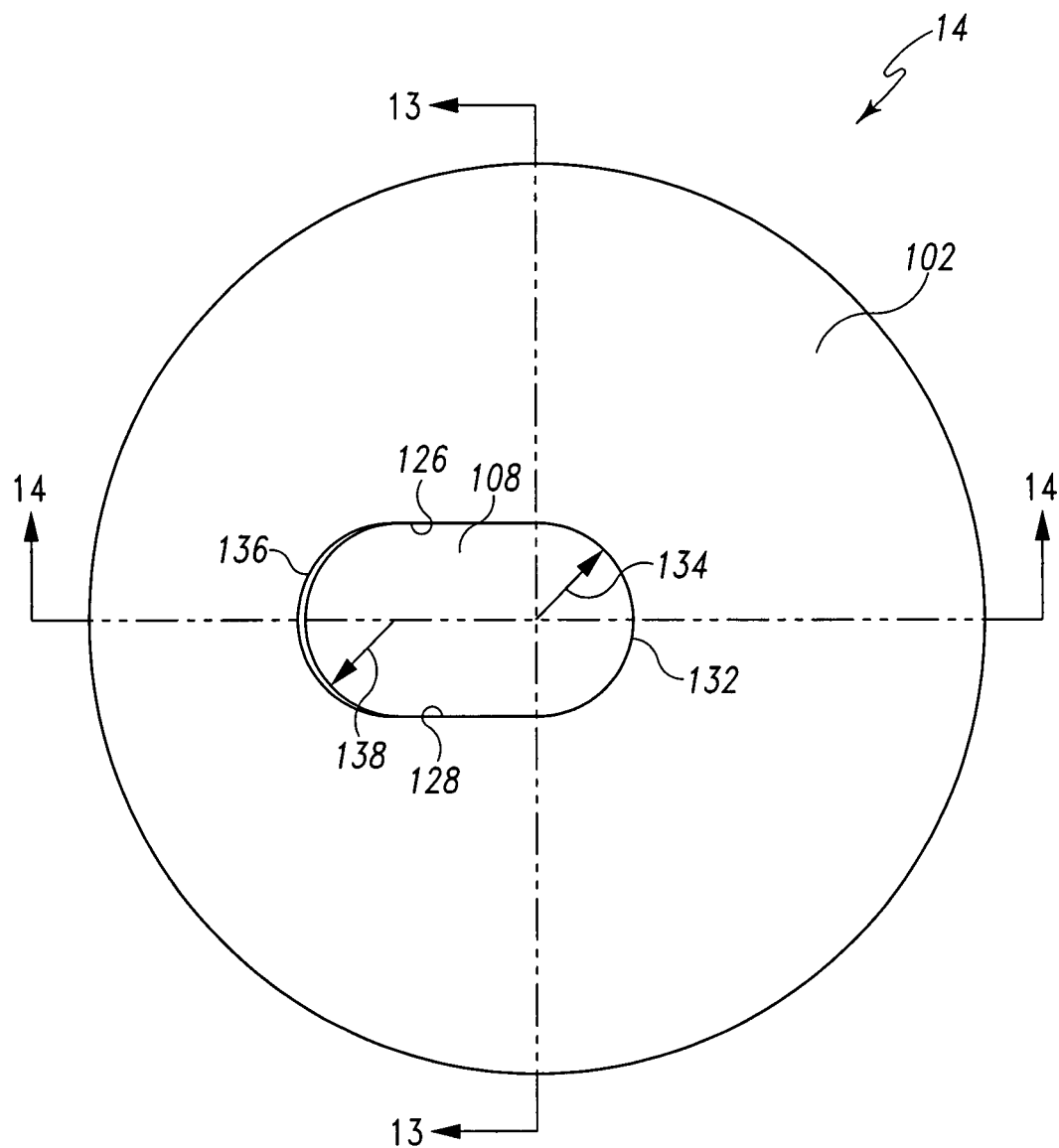
FIG. 10 is a plan view of the bearing positioner of FIG. 1.
Figure 11:
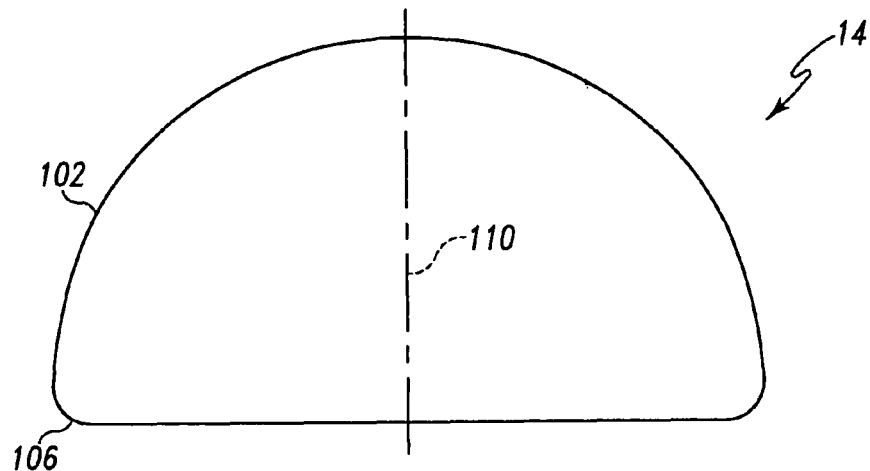
FIG. 11 is a side elevation view of the bearing positioner of FIG. 10.
Figure 12:
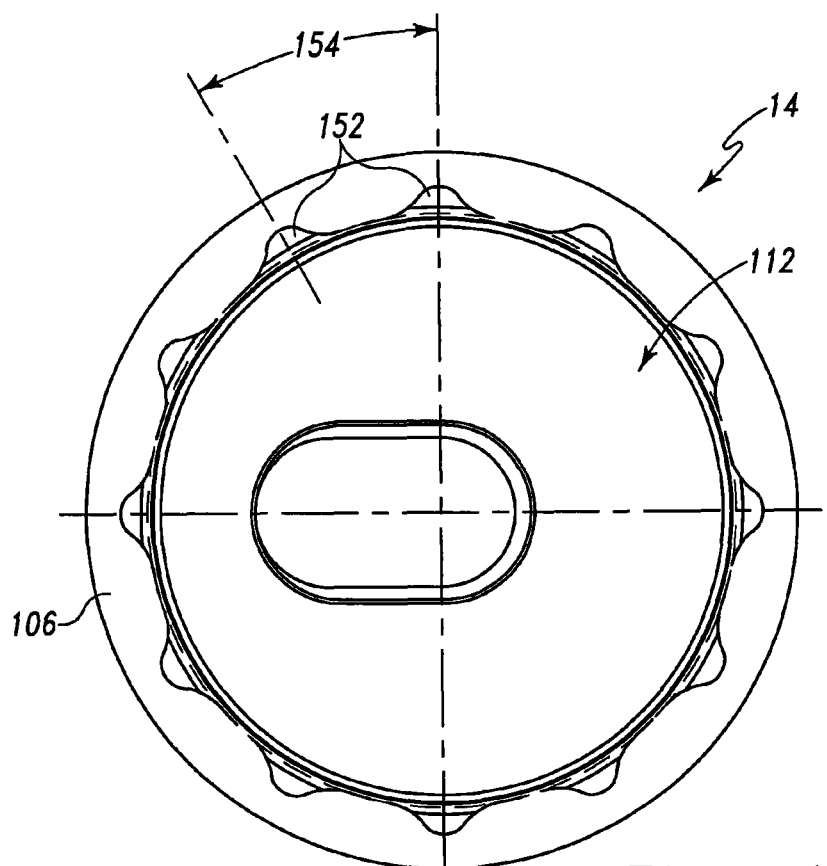
FIG. 12 is a plan view of the bearing positioner of FIG. 10.
Figure 14:
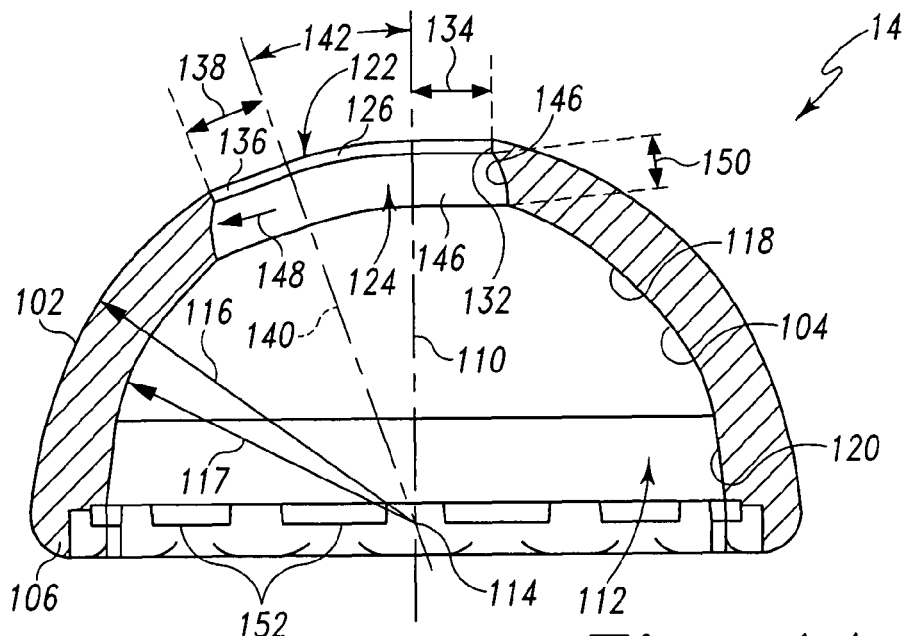
FIG. 14 is a sectional view taken along line 14-14 of the bearing positioner of FIG. 10.
Figure 13:
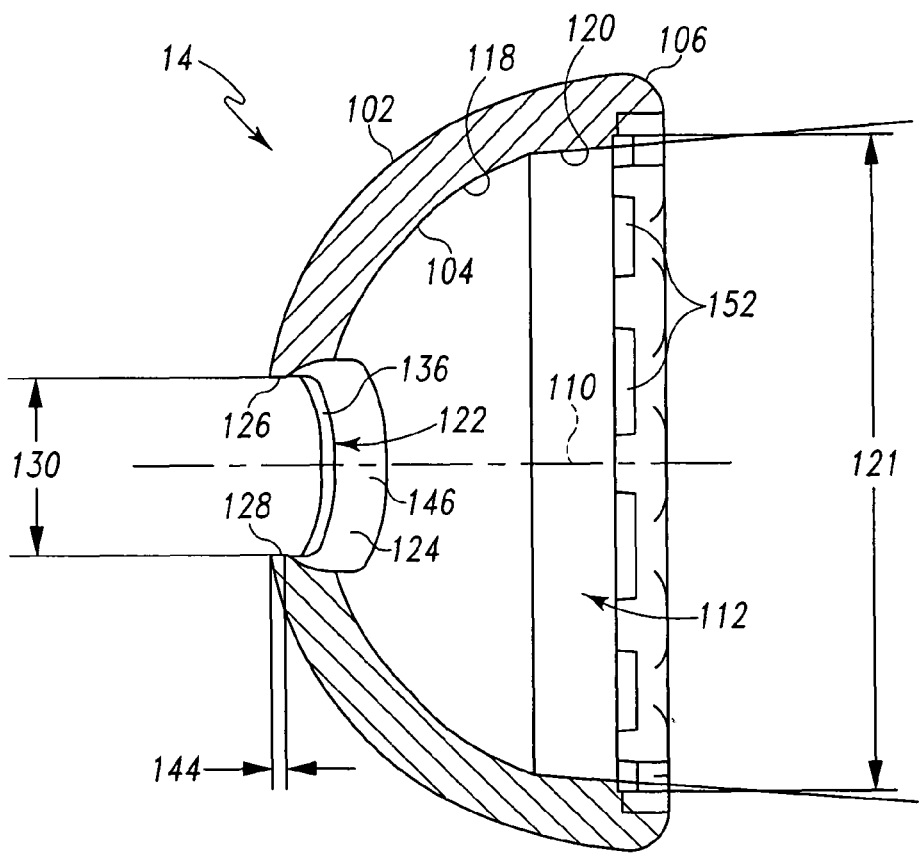
FIG. 13 is a sectional view taken along line 13-13 of the bearing positioner of FIG. 10.
Figure 16:
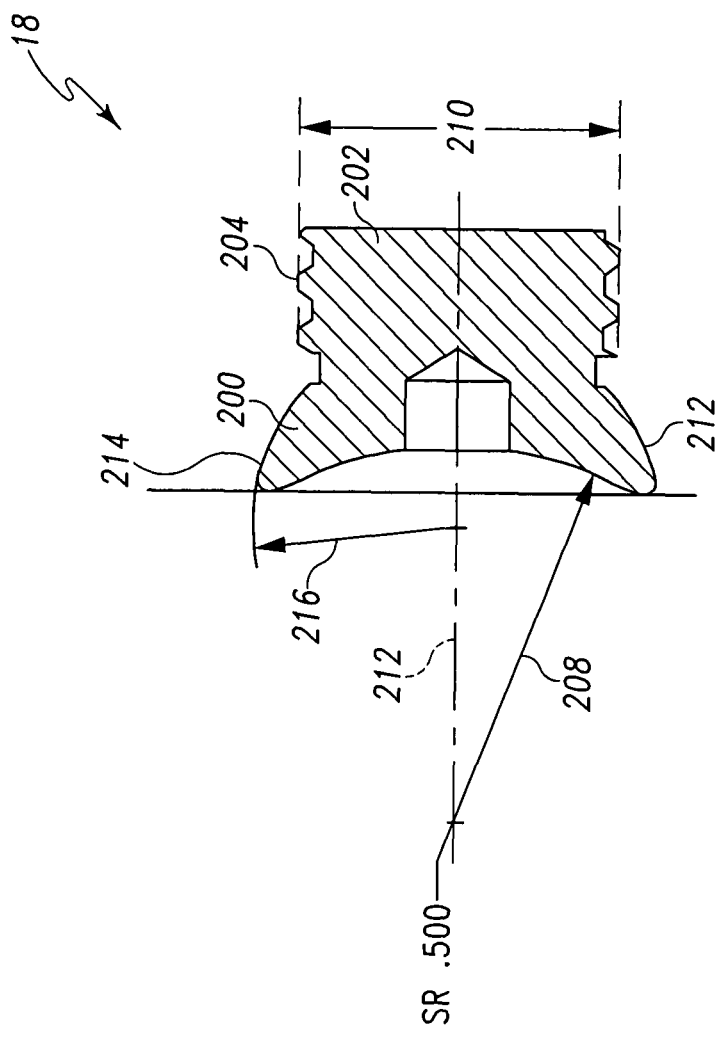
FIG. 16 is a sectional view taken along the line 16-16 of the screw of FIG. 15.
Figure 15:
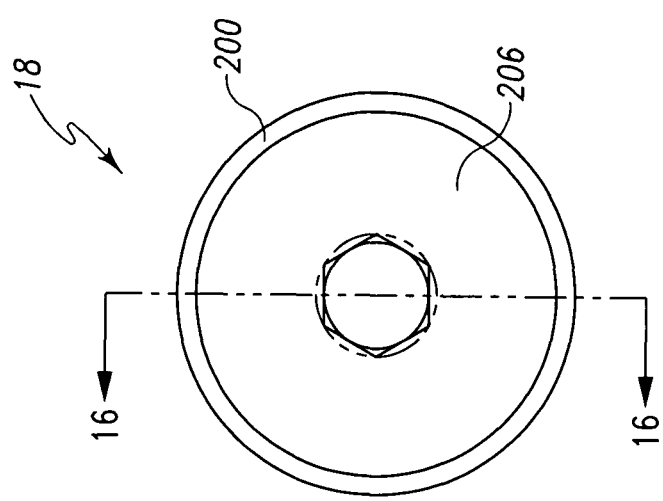
FIG. 15 is a plan view of the screw of the acetabular cup assembly of FIG. 1.

Thus the shaft 202 of the screw 18 and the end walls 132 and 134 of the shaft receiving slot 122 cooperate to limit the angulation of the bearing positioner 14 relative to the shell 12 to between a neutral position, as shown, for example, in FIG. 3, to a twenty degree angulated position, as shown for example in FIGS. 1 and 2. The side walls 126, 128 and end walls 132, 136 extend inwardly from the convex surface 102 of the bearing positioner 14 to a depth 144. Illustratively, the depth 144 is approximately 0.040 inches.

The head-receiving slot 124 of the screw-receiving slot 108 of the bearing positioner comprises a concavely curved side wall 146. The radius of curvature 148 of the concave wall 146 of the head-receiving slot 124 of the screw-receiving slot 108 of the bearing positioner 14 is approximately equal to the radius of curvature 216 of the convex side wall 214 of the head 200 of the screw 18. The curved side wall 146 extends between and couples the concave surface 104 and the fastener-receiving slot 122 of the bearing positioner 14. The head-receiving slot 124 has a depth 150 approximately equal to or greater than the maximum thickness 218 of the head 200 of the screw 18 so that the head 200 of the screw 18 does not interfere with positioning of the bearing 16 in the bearing positioner 14 when the screw 18 is used to secure the bearing positioner 14 to the shell 12.

The rim wall 106 and concave surface 104 are formed to include a plurality of radially extending orientation notches 152. In the illustrated embodiment, twelve orientation notches 152 extend into the rim wall 106 and concave surface 104 adjacent the junction of the rim wall 106 and concave surface 104. Each orientation notch 152 is equidistantly angularly displaced from each of its adjacent orientation notches 152. Thus, in the illustrated embodiment, each orientation notch 152 is displaced from each of its adjacent orientation notches 152 by an angle 154. Illustratively, angle 154 is approximately thirty degrees.

Each orientation notch 152 is configured to receive a radially extending triangular orientation flange 99 extending from the concave surface 92 of the bearing 16. The use of orientation notches 152 and flanges 99 is common in the prosthetic art and particularly in the acetabular cup assembly prosthetic art and will not be discussed in detail. Orientation notches and flanges are shown and described in U.S. Pat. Nos. 5,935,175; 5,571,198; and 5,782,928, the disclosures of which are incorporated herein by reference.

As shown, for example, in FIGS. 2, 3, 15 and 16, the screw 18 includes a head 200 and a shaft 202 on which a thread 204 is formed. As previously stated, the thread 204 is sized and configured to cooperate with the thread 84 of the attachment hole 80 so that screw 18 can be utilized to secure bearing positioner 14 to shell 12. The head 200 of the screw 18 includes a concave top surface 206, and a convexly curved side wall 214. The convexly curved side wall 214 extends between and couples the concave surface 206 of the head 200 to the shaft 202 of the screw 18. The entire screw 18 is formed concentrically (except for the threads 204) about a longitudinal axis 212. The concave face 206 of the head 200 has a radius of curvature 208 so that the surface lies below the concave surface 102 of the bearing positioner 14 when the screw 18 is received in the screw-receiving slot 108 of the bearing positioner 14 and the attachment hole 80 of the shell 12 and tightened. In the illustrated embodiment, the radius of curvature 208 of the concave surface 206 of the head 200 is approximately 0.500 inches. Thus, the head 200 of the screw 18 does not interfere with positioning of the bearing 16 within the bearing-receiving cavity 112 of the bearing positioner 14.

The convexly curved side wall 214 of the head 200 of the screw 18 exhibits a radius of curvature 216. The radius of curvature 216 is approximately equal to the radius of curvature 148 of the concave wall 146 of the head-receiving slot 124 of the screw-receiving slot 108 of the bearing positioner 14. Thus, when the screw 18 is received in the screw-receiving slot 108 and tightened, portions of the convex side wall 214 of the head 200 of the screw 18 engage the concavely curved wall 146 of the head-receiving slot 124 of the screw-receiving slot 108 of the bearing positioner 14 along contiguous surface areas. This aids in securely fastening the bearing positioner 14 in its selected orientation relative to the shell 12.

The shaft 202 of the screw has a diameter 210 slightly less than the displacement 130 between the side walls 126, 128 of the fastener-receiving slot 122 of the screw-receiving slot 108 of the bearing positioner 14. This allows the bearing positioner 14 to be angulated with respect to the shell 12 by sliding the shaft 202 of the screw 18 prior to tightening longitudinally within the fastener-receiving slot 122. This also facilitates rotation of the bearing positioner 14 about the screw 18 prior to tightening for rotational positioning of the bearing positioner 14 relative to the shell 12.

In the illustrated embodiment, the head 200 of the screw 18 has a maximum thickness 218. In the illustrated embodiment, the maximum thickness 218 is approximately 0.150 inches. The head of the screw 18 also has a diameter 220 which in the illustrated embodiment is approximately 0.535 inches. The head 200 of the screw 18 may be formed to include structure to facilitate rotation and tightening of the screw 18. In the illustrated embodiment, the head 200 of the screw 18 is formed to include a hex hole 224 formed concentrically about the axis 212. The hex hole 224 permits an instrument, such as an allen wrench or other hex shaped driver, to be utilized to tighten the screw 18.

The illustrated screw 18 has a maximum length 222 selected to permit the shaft 202 to extend sufficiently far into the attachment hole 80 of the shell 12 when the head 200 is received in the head-receiving slot 124 of the screw-receiving slot 108 of the bearing positioner 14 to allow the bearing positioner 14 to be secured in its desired position relative to the shell 12. In the illustrated embodiment, the maximum length 222 is approximately 0.0350 inches.

Referring to FIGS. 1-3, the bearing 16 includes a convex surface 90 that has a generally semispherical portion 89 and a taper wall portion 91. The taper wall portion 91 forms a male taper configured to cooperate with the female taper of the bearing positioner 14 to aid in securing the bearing 16 in the bearing positioner 14. Bearing 16 also includes a concave bearing surface 92 that defines an opening 94 sized to receive a prosthetic femoral ball (not shown). A rim 96 extends circumferentially around opening 94 of bearing 16. Bearing 16 is symmetrical. It is understood, however, that bearing 16 of the present invention may be a nonsymmetrical component. Bearing 16 is preferably made from a polymeric material such as ultra high molecular weight polyethylene (UHMWPE). Of course, bearing 16 could be made of other types of implantable bearing materials such as a metal material or a ceramic material. The illustrated bearing 16 is a neutral bearing of the type commonly available from DePuy Orthopedics as a component of their Pinnacle Acetabular Cup System™. Such a bearing 16 includes a Variable Interface Prosthesis (VIP) taper, which provides a locking mechanism for use with advanced hard bearing surfaces, such as the Ultamet™ Metal-on-Metal Articulation. The use of hard bearing surfaces holds the potential for reduced wear and greater longevity. If future revisions would be necessary, the VIP taper allows for exchange of the bearing 16 without exchanging a well-fixed shell 12.

The bearing 16 is fitted within the cavity 112 of the bearing positioner 14 in a conventional manner. For instance, the triangular orientation flanges 99 on the bearing 16 may be aligned with orientation notches 152 of the bearing positioner 14 most closely positioned to the desired rotational orientation of the bearing 16 with respect to the bearing positioner 14. The bearing 16 and bearing positioner 14 are locked together in a conventional manner. For instance, the taper wall 120 of the bearing positioner 14 and the taper wall portion 91 of the bearing 16, acting as female and male tapers, respectively, cooperate to hold bearing 16 in position relative to the bearing positioner 14. The male taper of the bearing 16 engages the female taper of the bearing positioner 14 and forms a locking mechanical connection therebetween. Taper walls 120, 91 may be a straight taper, as in FIGS. 2-3 and 13-14, or they may be as a curve of a conic section—circle, ellipse, parabola, hyperbola or the like. If taper of convex surface 90 of the bearing 16 is straight, taper of the concave surface 104 of the bearing positioner 14 is also straight.

The described male and female tapers are machine tapers that provide a connection that ensures and maintains accurate alignment between bearing positioner 14 and the bearing 16 and permits bearing positioner 14 and the bearing 16 to be separated for reconditioning or for substitution of other parts. Tapers may be a self-holding taper (i.e. self-locking) or a self-releasing taper.

In use, the shell 12 is oriented within the bone in such a way as to maximize potential for short term stability and long term fixation without regard to the position of the concave surface 22. The bearing positioner 14 is then mechanically locked into the shell 12 at an angular and rotational position relative to the shell 12 to orient the concave bearing face 92 of the bearing 16 to be received in the bearing positioner 14 at a desired position to closely simulate the anatomical structure of the patient into which the acetabular cup assembly 10 is being implanted. The bearing 16 mechanically locks into the bearing positioner 14. The bearing positioner 14 mechanically locks to the shell 12 and the shell 12 attaches to the acetabulum with or without the aid or one or more adjunct fixation devices such as screws, spikes, flanges, bubbles, etc. The shell 12 is oriented within the bone in such a way as to maximize potential for short term stability and long term fixation irrespective of the face 92 position. After the shell 12 is fixed to the bone, the bearing positioner 14 is attached to the shell 12 and oriented in such a way as to optimize stability of the artificial joint and then is mechanically locked to the shell 12. Next the appropriate bearing 16 is selected and seated in the bearing positioner 14.

Figure 17:
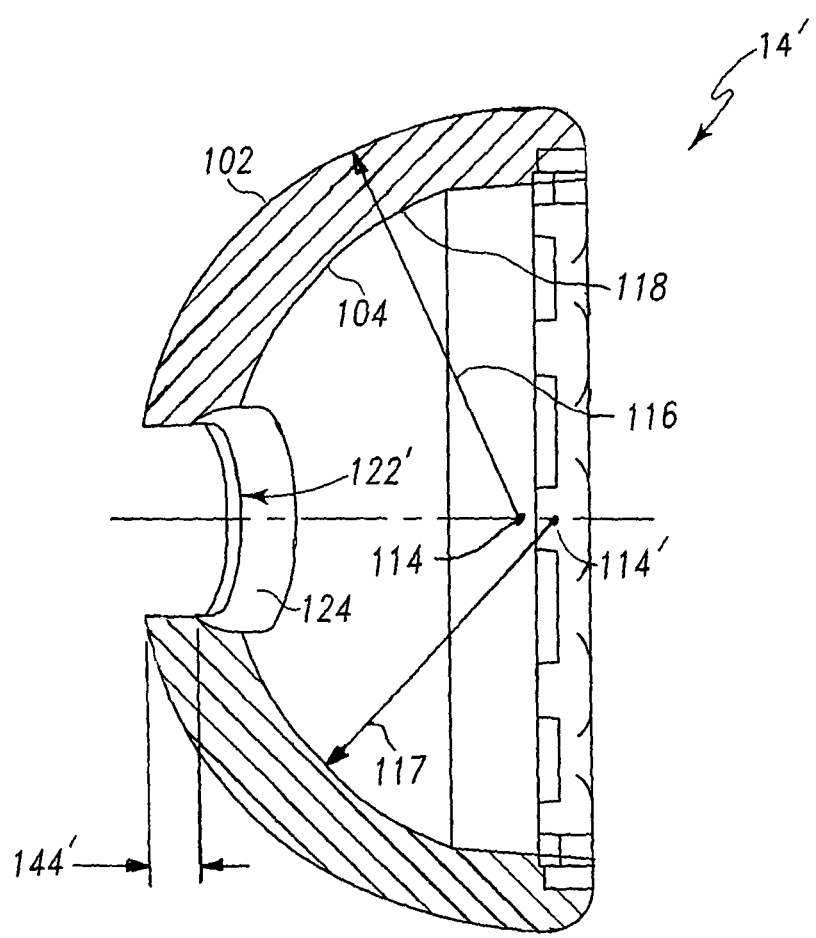
FIG. 17 is a sectional view of a bearing positioner similar to FIG. 13 in which the bearing positioner has been lateralized.

In addition to the adjustment of angular position accomplished as described above, the bearing positioner of the illustrated embodiments may also provide for adjustment of the center of articulation of the bearing within the positioner. It is thus contemplated that the bearing positioner may be lateralized so that the concave surface on which the bearing 16 articulates is shifted laterally relative to the outer surface that engages the shell 12. In one example shown in FIG. 17, a lateralized bearing positioner 14' includes an outer convex surface 102 and an inner concave surface 104 that are identical to the like surfaces on the positioner 14 shown in FIGS. 13 and 14. Similarly, the remaining engagement features of the bearing positioner can be the same as described above, such as the inner semispherical and tapered portions and orientation notches.

Importantly, the radius of curvature 117 of the semispherical portion 118 is unchanged after the lateralization of the bearing positioner 14'. However, the focus 114' of this radius of curvature 117 is offset from the focus 114 from which the radius of curvature 116 of the outer convex surface 102 is measured. This lateralization of the bearing positioner is also manifested in an increase in the depth 144' of the fastener-receiving slot 122', as well as the overall height of the positioner. It can thus be appreciated that the thickness of the bearing positioner is increased at the slot 122' to laterally offset the interior engagement features of the positioner 14'. It can be appreciated that the amount of lateralization shown in FIG. 17 has been exaggerated for clarity. In practice, alternative bearing positioners 14' may be provided with increasing heights in increments of 0.010 inches to accommodate subtle variations in joint anatomy.

The bearing positioner 14 can be oriented at any angle within a range (in the illustrated embodiment up to twenty degrees from a neutral position) relative to the shell 12 and can be oriented rotationally relative to the shell 12 in any position. The options for relative position between the bearing positioner 14 and the shell 12 can be infinite or can be predefined to a finite number of positions (such as every five degrees) within the scope of the disclosure.

In the first embodiment of the acetabular cup assembly 10, the concave surface 22 of the shell 12 and the convex surface 102 of the bearing positioner 14 are generally semispherical and hemispherical, respectively, in shape. The shell 12 contains a threaded apex attachment hole 80. The bearing positioner 14 contains an apex slot hole 108 that is elongated to one side of the axis 110 sufficiently to provide the desired amount of relative angular position between the shell 12 and the bearing positioner 14. The screw 18 passes through the screw-receiving slot 108 in the bearing positioner 14 and into the attachment hole 80 in the shell 12 to fasten the bearing positioner 14 to the shell 12. The bearing positioner 14 is able to angulate as allowed by the elongated slot 108 and can be positioned rotationally by rotating the bearing positioner 14 about the head 200 of the screw 18.

The disclosed device 10 allows revision of well fixed cups with inadequate face positioning without disrupting the shell/bone interface and allows positioning of a new acetabular reconstructive device 10 where most advantageous for bone fixation and positioning of the bearing face 92 in the optimum position for stability, each independent of the other.

In this specification and in the claims, the words "hemispherical" and "semispherical" are intended to cover the hemispherical and semispherical ranges conventionally used in acetabular and glenoid shells, liners, and cup bearings including less than hemispherical and, in some cases, more than hemispherical.

Figure 18:
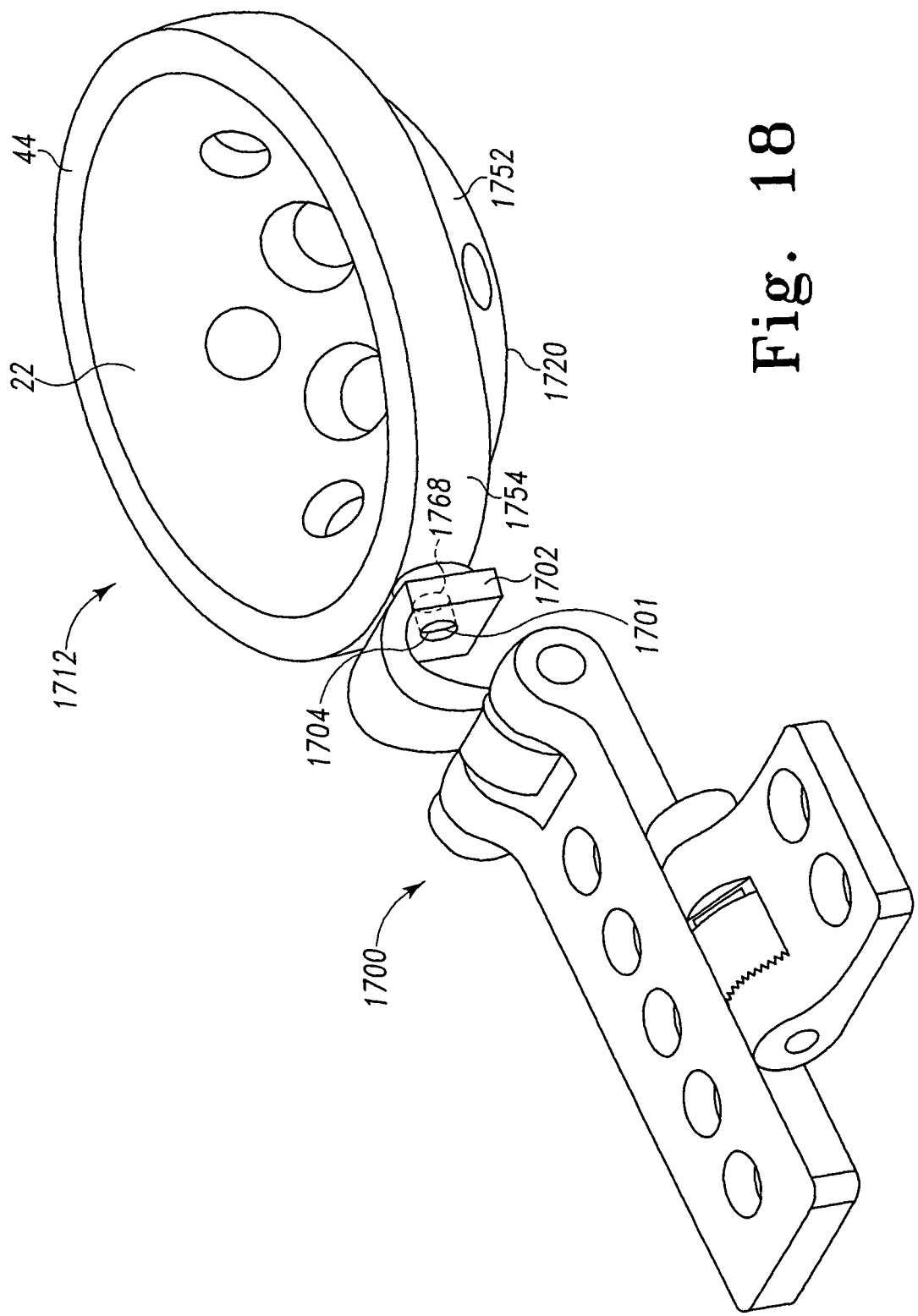
FIG. 18 is a perspective view of a second embodiment of a shell for use with the acetabular cup assembly of FIG. 1 and an attachment bracket configured to facilitate attachment of the shell to the hip of a patient.

An alternative embodiment of shell 1712 is illustrated in FIG. 18. Shell 1712 is substantially similar to shell 12 and thus identical components will not be described in detail. Shell 1712 includes a bone facing surface 1752 that does not include the lips 58 and 60 that define the attachment channel 40 present in shell 12. Also, illustrated shell 1712 includes a single attachment hole 1768 (obscured by flange 1702) for attachment of an adjunct attachment device 1700 thereto. The illustrated adjunct attachment device 1700 is of a type commonly used with acetabular prosthesis to facilitate attachment of the prosthesis to the hip of a patient in a location optimal for stable attachment of the shell 12 in the acetabulum. It is within the scope of the disclosure for other known and to be discovered adjunct attachment devices 1700 to be utilized either as is or through slight modification with the disclosed shells 12, 1712 and 1812 of the acetabular cup assemblies 10, 1810 disclosed herein.

FIG. 19 is a perspective view of a second embodiment of an acetabular cup assembly 1810. Like acetabular cup assembly 10, acetabular cup assembly 1810 facilitates attachment of the shell component 1812 to the patient in an optimal location to facilitate stability of the assembly 1810 without regard to the desired location of the bearing face 92 of the bearing 1816. The illustrated acetabular cup assembly 1810 includes a shell 1812, a bearing positioner 1814, a bearing 1816 and a set screw 1818. Bearing 1816 is very similar to bearing 16 except that bearing 16 is a neutral bearing whereas bearing 1816 is configured to provide medial or lateral alteration of the bearing face 1892. Bearing 1816 is of the type of bearing commonly available from DePuy Orthopedics as a component of their Pinnacle Acetabular Cup System™

Shell 1812 is somewhat similar to shell 12. While shell 1812 is not illustrated as including any attachment feature 32, it is within the scope of the disclosure for shell 1812 to be provided with any of the attachment features 32 discussed above with regard to shell 12 or shell 1712. Shell 1812 includes diametrically opposed orientation flanges 1817, 1819 extending distally from the rim 1844 of the shell 1812. Illustratively, the inner surfaces 1821 of the orientation flanges 1817, 1819 exhibit a radius of curvature identical to the radius of curvature 28 (not shown in FIG. 19 but similar to that shown in FIGS. 5 and 6) of the concave surface 22 (not shown in FIG. 19 but similar to that shown in FIGS. 5 and 6) of shell 1812.

Each flange 1817, 1819 includes a slot 1823 extending equatorially partially along the length of the flange 1817, 1819. Each slot 1823 is configured to receive a tang 1911 (only one of which is visible in FIG. 19) extending from the convex surface 102 of the bearing positioner 1814. Each tang 1911 extends radially from the convex surface 102 of the bearing positioner 14 and is diametrically opposed to the other tang 1911. The slots 1823 in flanges 1817, 1819 and tangs 1911 are configured to allow the tangs 1911 to move longitudinally within the slots 1823 to facilitate angular adjustment of the bearing positioner 1814 relative to the shell 1812.

Due to the presence of the slots 1823, flanges 1817, 1819 and tangs 1911, the bearing positioner 1814 can not be positioned rotationally relative to the shell 1812. Rotational positioning of the bearing positioner 1814 can be accomplished through rotation of the combined shell 1812 and bearing positioner 1814 subassembly.

A flange 1825 extends distally from the rim 44 of the shell 1812. The flange 1825 is configured to include a set screw-receiving hole 1827 extending therethrough within which a set screw 1818 is received. Upon angular rotation of the bearing positioner 1814 relative to the shell 1812, the set screw 1818 is tightened to fix the relative positions of the bearing positioner 1814 and shell 1812.

Those skilled in the art will recognize that many currently available shells for acetabular cup systems include an apex hole, either configured for receipt of a bone screw or for attaching a bearing directly or indirectly to the shell and a semispherical or hemispherical concave surface. Thus, using an appropriately configured screw capable of being secured within the apex hole of an existing prior art shell, the disclosed bearing positioner 14 and bearing 16 can be utilized within the scope of the disclosure to replace a worn or misaligned bearing received in such a prior art shell. By utilizing the disclosed bearing positioner 14 and bearing 16 to replace a worn or misaligned bearing, the acetabular component of an existing hip prosthesis can be refurbished without the need of removing the prior art shell.

Those skilled in the art will recognize that bearing 16 and bearing 1816 are interchangeable and either may be utilized with any of the bearing positioners 14, 1814 described herein within the scope of the disclosure. Acetabular cup assembly 1810 is utilized in much the same manner as described above with regard to acetabular cup assembly 10.

Although the invention has been described in detail with reference to certain preferred embodiments, variations and modifications exist within the scope and spirit of the invention as described and defined in the following claims. For example, while the prosthetic cup assembly is disclosed in the context of a hip prosthesis, it has utility in other locations within a patient's body.

What is claimed is:

1. A bearing positioner for use with a prosthetic component, a fastener, and a bearing, the bearing having a convex surface and an oppositely facing bearing surface configured to bear against a first bone of a joint or prosthetic replacement for a portion of a first bone; the prosthetic component configured for attachment to a second bone of the joint, the prosthetic component includes a bone facing surface configured to face the second bone and a concave surface facing away from said bone facing surface and defining a cavity, said bearing positioner comprising:

an external convex surface defined at a first spherical radius from a first focus and having a shape configured to be received in said cavity in multiple orientations and to bear and be secured against said concave surface of the prosthetic component when in any orientation selected from said multiple orientations;

an internal concave surface defined at a second spherical radius from a second focus and defining a bearing-receiving cavity configured to receive a portion of said convex surface of the bearing therein and configured to orient said bearing surface of said bearing to bear against the first bone of the joint or the prosthetic replacement for the first bone when said external convex surface of said bearing positioner is secured in an orientation selected from said multiple orientations, wherein the second focus is offset from the first focus;
a locking member configured to rotationally lock the bearing when the portion of the convex surface of the bearing is received in the bearing-receiving cavity; and
a rim surface extending between and coupling said external convex surface and said internal concave surface, an elongated slot displaced from said rim and extending between and coupling said external convex surface and said internal concave surface and configured to engage the fastener having a threaded shaft configured to extend through said slot and to be received in a threaded hole in the prosthetic component.

2. The bearing positioner of claim 1, wherein said first focus is on an axis of symmetry of said bearing positioner and said second focus is on the axis of symmetry of said bearing positioner and said second spherical radius is less than the first spherical radius.

3. The bearing positioner of claim 2, wherein the axis of symmetry of said bearing positioner extends through said slot.

4. The bearing positioner of claim 2, wherein said second focus is laterally offset from said first focus away from said external convex surface along the axis of symmetry of said bearing positioner.

5. The bearing positioner of claim 2, wherein said multiple orientations include multiple angular orientations of said bearing positioner relative to the prosthetic component and multiple rotational orientations of said bearing positioner relative to the prosthetic component.

6. An acetabular prosthetic device for attachment to a hip comprising:
a shell configured for attachment to the hip and including a concave surface defining a cavity configured to face away from the hip;
a bearing positioner including a convex surface configured to be received within said cavity at multiple angular positions relative to said shell, and a concave surface facing in the opposite direction as the convex surface and defining a bearing-receiving cavity, wherein the convex surface is defined at a first spherical radius from a first focus and the concave surface is defined at a second spherical radius from a second focus, the second focus offset from the first focus;
a position fixation device configured to affix said bearing positioner to said shell in a selected one of said multiple angular positions; and
a bearing configured to rotationally lock with the bearing positioner and having a convex surface and an oppositely facing concave surface defining a bearing cavity for receiving a femoral head or a head of a prosthetic component replacing at least a portion of a femoral head and configured to allow the femoral head or head of a prosthetic component to articulate therein, wherein said convex surface of said bearing has a size and shape conforming to the size and shape of said concave surface of said bearing-receiving cavity to facilitate receipt of a portion of said convex surface of said bearing therein.

7. The device of claim 6, wherein said position fixation device includes a component of said shell and a component of said bearing positioner.

8. The device of claim 7, wherein said position fixation device includes a fastener having a shaft and an enlarged head, said component of said shell includes a hole sized to receive said shaft of said fastener and said component of said bearing positioner includes a slot having a length greater than a lateral dimension of said shaft so that prior to fixation of said bearing positioner to said shell said shaft can move along the length of said slot.

9. The device of claim 8, wherein said shaft of said fastener includes a screw thread, said hole in said shell is threaded with a screw thread configured to cooperate with said screw thread of said fastener to facilitate tightening of said fastener, said slot in said bearing positioner includes a portion adjacent said convex surface of said bearing positioner configured to allow said shaft, but not said head, of said fastener to pass therethrough and a portion adjacent said concave surface of said bearing positioner configured to receive said head therein and having a wall configured to engage said head upon tightening of said screw to lock said bearing positioner in a selected one of said multiple angular positions.

10. The device of claim 6, wherein said concave surface of said shell includes a semispherical portion having a radius of curvature substantially similar to the second spherical radius of said concave surface of said shell.

11. A method of assembling a prosthetic component assembly, comprising:
(a) providing a shell having a cavity with an inner surface, the inner surface having a shape;
(b) providing a bearing positioner having an outer surface with a shape corresponding to the shape of the inner surface of the shell and an oppositely facing concave surface defining a bearing-receiving cavity, wherein the outer surface of the bearing positioner is defined at a spherical radius from a first focus and the concave surface is defined at a spherical radius from a second focus, by selecting a bearing positioner from among a plurality of bearing positioners each having a different lateral offset between the first and second focus;
(c) inserting the bearing positioner into the shell with at least a portion of the outer surface in contact with the inner surface of the shell;
(d) then angulating the bearing positioner relative to the shell to position the bearing positioner in a desired angular relationship relative to the shell;
(e) securing the bearing positioner to the shell in the desired angular relationship;
(f) providing a bearing having a convex surface configured for receipt in the bearing-receiving cavity and an oppositely facing bearing surface configured for articulating engagement with a head of a bone or a prosthetic replacement;
(g) inserting the bearing into the bearing-receiving cavity after securing the bearing positioner to the shell so that at least a portion of the convex surface of the bearing engages at least a portion of the concave surface of the bearing positioner;
(h) rotationally orienting the bearing within the bearing positioner to optimally position the bearing for articulation with the head of the bone or prosthetic replacement; and
(i) securing the bearing to the bearing positioner at the optimal position.

12. The method of claim 11, further comprising rotating the bearing positioner relative to the shell after inserting the bearing positioner in the shell to position the bearing positioner in a desired rotational relationship relative to the shell and wherein the securing step includes securing the bearing positioner to the shell in the desired rotational relationship relative to the shell.

13. The method of claim 11, further comprising securing the shell to a hip of a patient prior to securing the bearing positioner to the shell.

\* \* \* \* \*